United States Patent [19]

Ansted

[11] 4,327,716
[45] May 4, 1982

[54] EMERGENCY STABILIZER FOR AN IMPALEMENT IN THE HUMAN BODY

[76] Inventor: Walter A. Ansted, 1325 Suffolk Ave., Westchester, Ill. 60153

[21] Appl. No.: 194,762

[22] Filed: Oct. 6, 1980

[51] Int. Cl.³ .............................................. A61F 13/00
[52] U.S. Cl. .................................................... 128/133
[58] Field of Search ............... 128/133, DIG. 26, 348, 128/349, 214 R

[56] References Cited

U.S. PATENT DOCUMENTS

| | | | |
|---|---|---|---|
| 3,422,817 | 1/1969 | Mishkin et al. | 128/133 X |
| 3,568,679 | 3/1971 | Reif | 128/349 |
| 3,834,380 | 9/1974 | Boyd | 128/133 |
| 3,918,446 | 11/1975 | Buttaravoli | 128/133 |
| 3,957,048 | 5/1976 | Jacobs | 128/214 R |
| 4,040,427 | 8/1977 | Winnie | 128/348 |

FOREIGN PATENT DOCUMENTS 653436 11/1937 Fed. Rep. of Germany ... 128/DIG. 26

*Primary Examiner*—John D. Yasko
*Attorney, Agent, or Firm*—William A. Snow

[57] ABSTRACT

An emergency means to stabilize an impaled object unintentionally entering the human body with portions of the projectile extending outside of the body so as to prevent further damage internally in the body. Also, such means may be used to wrap around the body of a person having fractured ribs.

4 Claims, 13 Drawing Figures

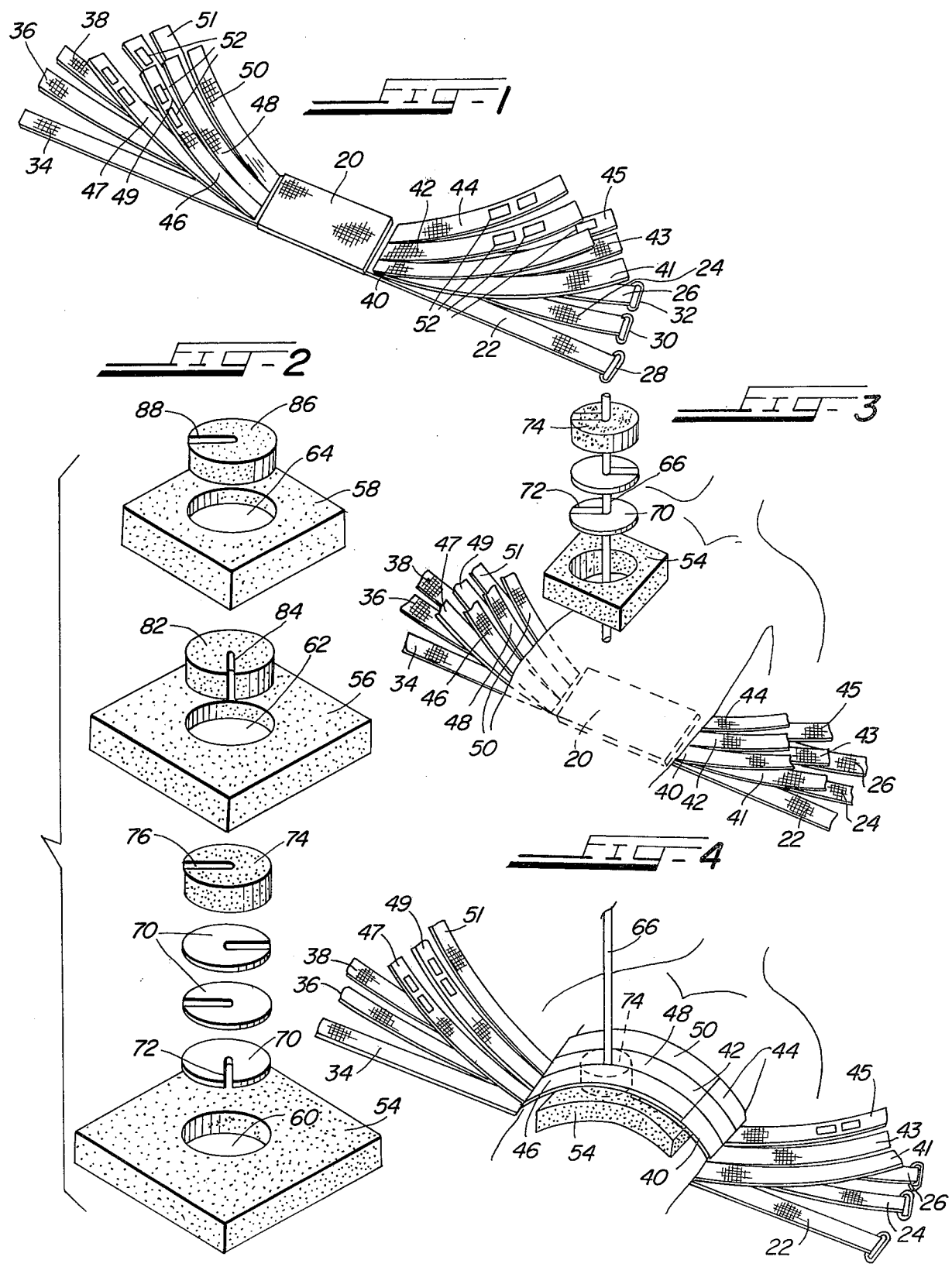

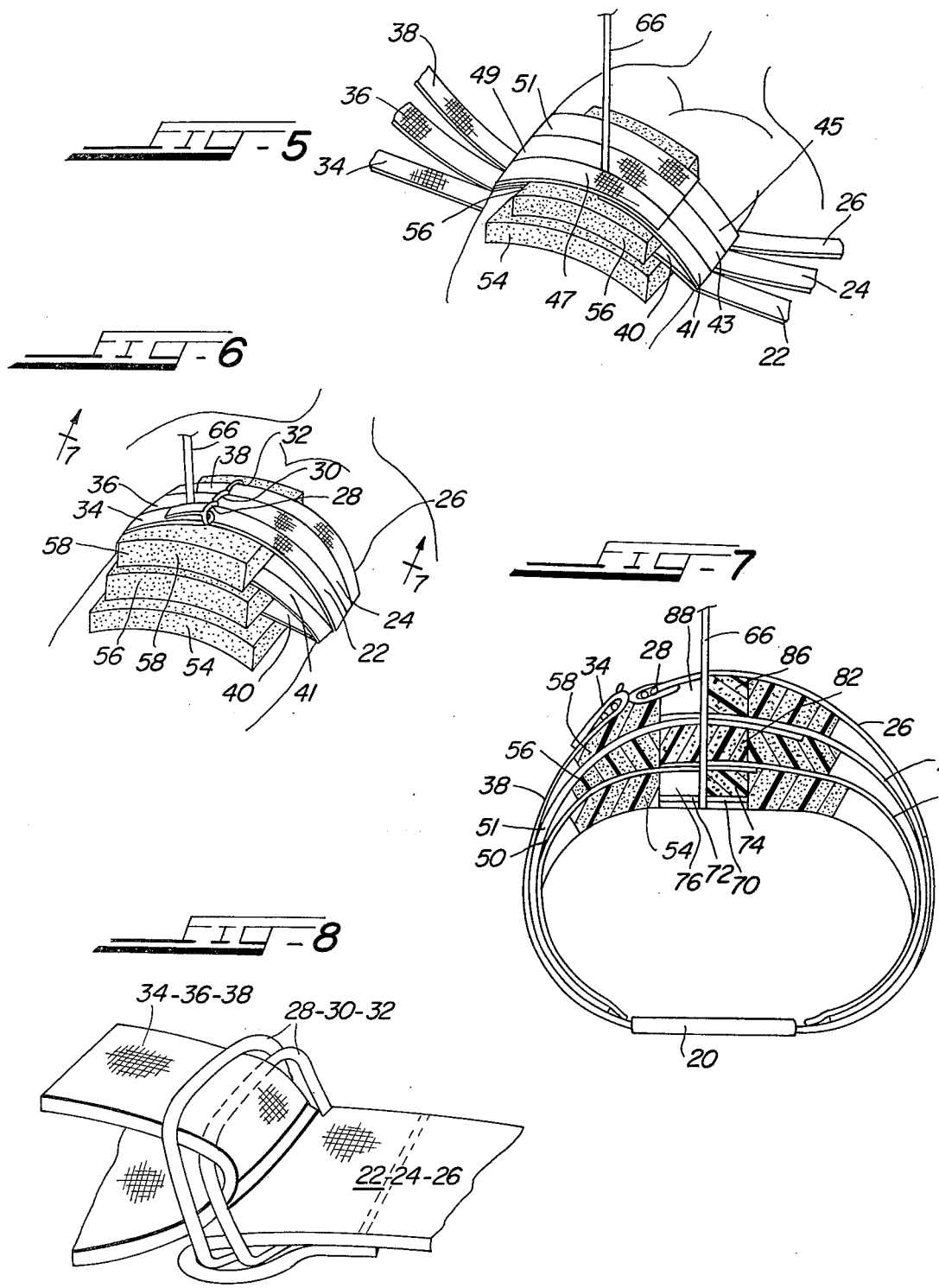

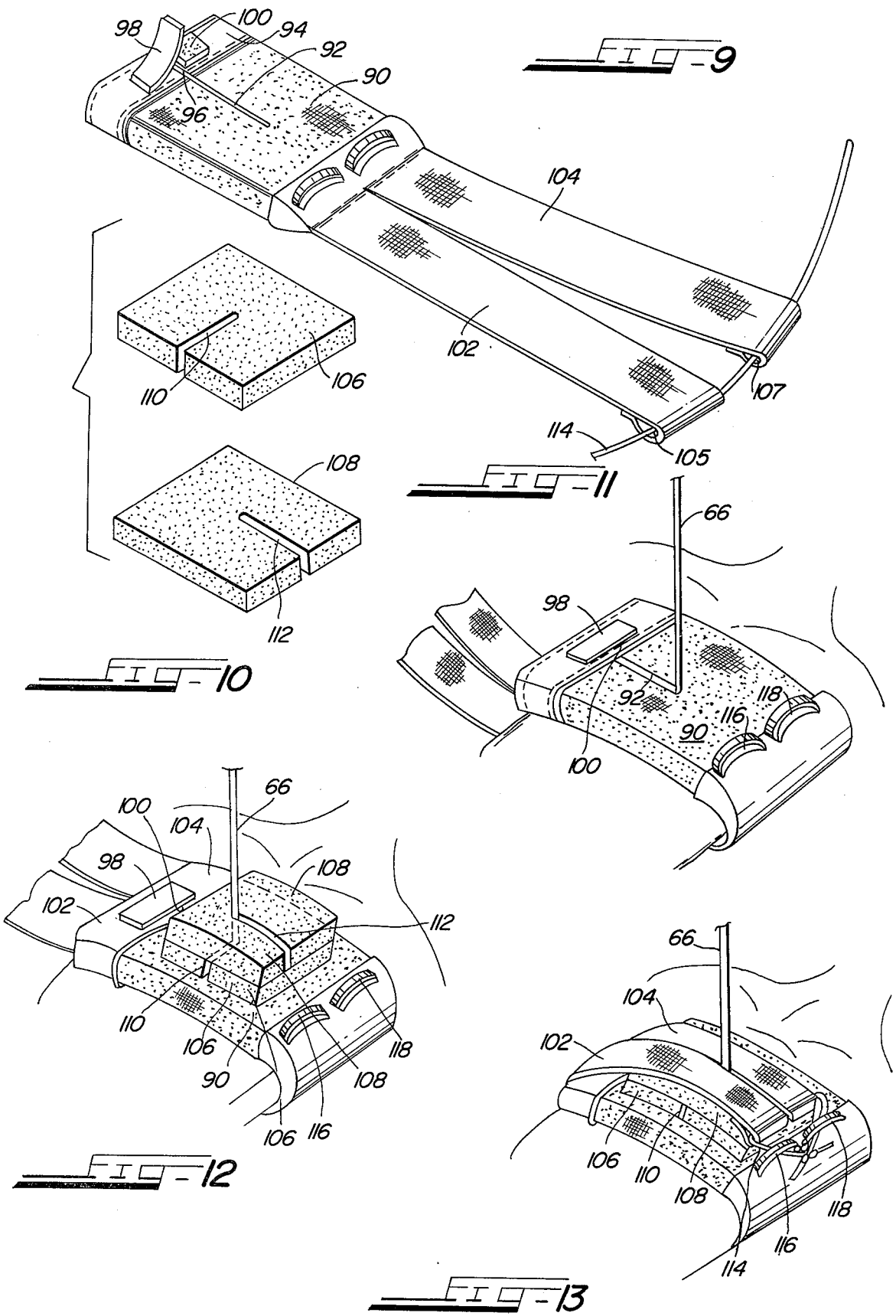

EMERGENCY STABILIZER FOR AN IMPALEMENT IN THE HUMAN BODY

BACKGROUND OF THE INVENTION

Many skiing accidents have occurred on the slopes when persons fall and the ski pole breaks. Since the ski pole is more-or-less anchored to the skier's wrist by a strap, in falling and tumbling down the slopes the ragged edge of the pole or the tip of the pole may, and on many occasions does, impale itself in the body of the skier. It then becomes necessary to stabilize the pole in place in the body to prevent further physical damage to the skier. Also, careless use of arrows from a bow may impale the arrow in the human body. The same stabilization as described above is required. There are many industrial accidents where persons are impaled with an object. It was to help prevent additional internal injury to persons having been impaled with an object that the present invention was conceived.

SUMMARY OF THE INVENTION

An emergency apparatus to surround the impaled object in the body of a human being wherein one or more clefts, in thick, soft articles are placed around the impaling object and anchored to stabilize the impaled object and prevent further internal damage before the person reaches a hospital. The articles may also be used around a body having cracked or broken ribs to stabilize them prior to removal to a hospital and prevent additional internal injury.

BRIEF DESCRIPTION OF THE DRAWINGS

FIG. 1 is a perspective view of the base and a series of anchoring and stabilizing straps;

FIG. 2 is an exploded perspective view of the soft pliable material placed around the impaled object and placed on a person's body;

FIG. 3 is an exploded perspective view disclosing how the devices shown in FIGS. 1 and 2 are assembled around the impaled object in a body;

FIG. 4 is a perspective view with the first three stabilizing straps in place over the device of FIG. 2;

FIG. 5 is a perspective view similar to FIG. 4 but showing the second set of stabilizing straps in place over additional soft pliable pads;

FIG. 6 is a perspective view similar to FIG. 5 but showing the final latching or anchoring belt straps in place to keep the impaled object from laterally shifting;

FIG. 7 is a cross-sectional view taken on the line 7—7 of FIG. 6;

FIG. 8 is a perspective view of the latching members taken on the circle of FIG. 6;

FIG. 9 is a perspective view of a modified form of anchoring strap secured to the soft, pliable thick base pad of the invention;

FIG. 10 is an exploded perspective view of the additional thick pads cleft edgewise and used with the device of FIG. 9;

FIG. 11 is a perspective view showing the device of FIG. 9 placed on the body of a person in position with an impaled object in place in the pad;

FIG. 12 is a perspective view showing the enlarged pads in position over the base pad shown in FIG. 11; and FIG. 13 is a perspective view showing the anchoring straps in place over the pads of FIG. 12 and stabilizing the impaled object.

DETAILED DESCRIPTION OF THE DRAWINGS

The device of the preferred embodiment shown in FIGS. 1 through 8 comprises a base member 20 preferably made of heavy fabric having three separate anchoring straps 22, 24, 26 secured thereto and extending on both sides of the base 20. One end of each of the straps has pairs of latching members 28, 30, 32 secured thereto for latching with the opposite ends of the straps 34, 36, 38, respectively, in the manner shown in FIG. 8, or any other suitable manner.

Three stabilizing fabric straps 40, 42, 44 are each anchored to the top of each one of the anchoring straps 28, 30 and 32, respectively, adjacent the base pad 20 and corresponding straps 46, 48 and 50 are each also anchored on top of straps 34, 36, 38, respectively, and adjacent the opposite side of the base pad 20. The free ends of the straps 40 to 50 have appropriate Velcro strips 52 secured thereto. Another series of fabric stabilizing straps 41, 43, 45 are secured to the straps 22, 24, 26, respectively, behind the securement of the stabilizing straps 40, 42, 44. Corresponding stabilizing straps 47, 49, 51 are secured to the straps 34, 36, 38, respectively, but slightly beyond where the straps 46, 48, 50 are anchored. All of the stabilizing straps are provided with a Velcro fastening 52.

As shown in FIG. 2, three thick, relatively large, flexible pads 54, 56, 58, preferably of sponge foam, are each provided with circular medial openings 60, 62, 64, respectively.

The base pad, in the case of a person having been impaled in the front section of his body, is carefully slid under his torso so that the base pad 20 is substantially directly below and in line with the impaled object, as seen in broken lines in FIG. 3, with all the straps extending outwardly away from the body, as shown.

If the tip of a ski pole is impaled in the body, the non-flexible circular members, preferably of cardboard, plastic or the like 70, with their clefts 72 are inserted around the tip of the ski pole below the basket and to the lower end of the same to prevent further penetration. In the event of any impaled object having a shoulder, the same procedure as described herein is followed. The clefts 72 are placed at 90° from each other and the members 72 act as shims. Then the thick pad 54 having a circular medial opening 60 is placed over the impaling object, the basket and members 70 down to the body of the person impaled. The opening 60 is slightly larger than the diameter of the basket.

Then, in the cases stated above, a circular, flexible insert pad 74 of the same material as the pad 54, having a cleft 76 of substantially the same diameter as that of the opening 60, is inserted in the opening 60 down to the body of the impaled person. The cleft lies at a 90° angle to the last cleft in the uppermost disk 70. Then the series of stabilizing straps 40 through 50 are placed over the pad 54 under slight downward pressure and latched together with the Velcro strips 52. This is shown in FIG. 4.

If necessary for stability, an additional large, thick, flexible pad 80, identical to pad 54, is placed on top of pad 54 and a second soft resilient pad 82, identical to pad 74, is inserted and seated in the opening 62 with the cleft 84 positioned at right angles to the cleft 76 in pad 74. Then the second series of stabilizing straps 41, 43, 45 and 47, 49 and 51 are placed over the pad 56 and pressure latched with the Velcro strips. This is shown in FIG. 5.

Then, if required for stability, a third large pad 58, identical to pads 54 and 56, is placed over pad 56 with its insert pad 86 having its cleft 88 positioned at right angles to the cleft 84. All the foregoing pads are relatively thick.

Then the anchoring straps 22, 24 and 26 and their opposite straps 34, 36 and 38, respectively, are anchored about the entire unit hereinabove described and fastened securely by the latching means 28, 30, 32 in the manner shown in FIG. 8. The assembled unit is seen in FIGS. 6 and 7.

Now the impaled object is substantially immovable and the person is ready to go to a hospital.

In the event the impaled object is quite lengthy, the upper part of it may be appropriately removed by cutting, etc. above the stabilized unit, as seen in FIG. 7.

In the modification shown in FIGS. 9 through 13, a flexible base pad 90 of foam plastic is employed having a cleft 92 with a fabric strap 94 anchored around to one end, split as at 96 and having comparable Velcro strips 98, 100 on the fabric as shown on each side of the split 96.

A pair of elongated fabric binding straps 102 and 104 are secured at one ene to the free edge of the pad 90 opposite strap 94. The free ends of the straps 102 and 104 are provided with elongated pockets 105, 107.

A pair of thick, soft, flexible pads 106, 108, preferably of foam plastic, each has an endwise cleft therein at 110 and 112, respectively.

In use, the straps 102, 104 are placed under the body, as shown in FIG. 11, and the cleft 92 may be placed right up to the closed end and against the impaled piece and the Velcro straps 98, 100 are fastened together. Then the pad 106 is placed on the base pad 90, with the impaled piece in the cleft 110. The cleft 110 is positioned at 90° from the direction of the cleft 92, all as shown in FIG. 12.

Then the pad 108, if necessary, is placed on the pad 106 with the impaled device in the cleft 112 and with the cleft positioned 90° from the cleft 92. The impaled device may be positioned at the closed end of the clefts, as shown in FIG. 12.

Then the fabric straps 102, 104 are placed over the entire unit hereinabove described and the tie 114 in the loops 105, 107 is inserted through the loops 116, 118 and securely fastened, as shown in FIG. 13. The straps will exert downward pressure on the pads to stabilize the impaled piece 68.

It should be obvious that if the impaling object is very long, it may be cut off at or above the top anchoring straps.

It should also be obvious that in the event one or more ribs are fractured or broken, both of the embodiments of this invention may be used to stabilize the area of the fracture prior to transportation to the hospital and help to prevent further internal damage.

It should be obvious from the foregoing that this invention as described may be used no matter where the impaled device enters the human body.

It should also be borne in mind that when an object having no basket, as in a ski pole or a shoulder on the impaling object, the disks or shims 70 are not required.

It will be understood that numerous details may be altered or omitted without departing from the spirit of the invention as defined by the following claims.

I claim:

1. A stabilizing device for impaled objects having a shoulder entering the human body comprising:
   (a) a base pad;
   (b) a series of anchoring straps secured to and extending from opposite sides of said base pad;
   (c) a series of stabilizing straps having one end of each secured to each of said anchoring straps adjacent the base pad and the other end having latching means thereon;
   (d) a lower, soft, pliable, thick pad to lie against the body having an enlarged medial opening therein in which the impaled object projects;
   (e) a series of thin, nonpliable disks each having a cleft therein for placement around the impaled object with each cleft placed 90° from the other and positioned below the shoulder of the impaled object;
   (f) a soft, pliable, thick, circular insert pad having a cleft therein positioned in said medial opening with the impaled object seated in said cleft;
   (g) a second thick, enlarged, soft, pliable pad having an enlarged medial opening therein to seat on said lower pad; and
   (h) a small, thick, pliable, circular insert pad having a cleft therein positioned in said opening in said second pad with the impaled object in said cleft;
   said stabilizing straps secured together above said second pad, and the anchoring straps secured thereover exerting pressure towards the body to stabilize the impaled object.

2. The device according to claim 1 wherein a third thick, enlarged, soft pad having an enlarged medial opening is placed around the impaled object and a small, thick, circular, pliable insert pad, having a cleft therein, is placed in said third pad opening and said third pad is anchored to said second pad by said stabilizing and anchoring straps.

3. In a device for stabilizing an impaled object in a human body comprising:
   (a) a relatively thick, soft, flexible base pad cleft endwise;
   (b) a fabric strap secured around one end of said base pad and split at the cleft therein;
   (c) means on said fabric for securing said split fabric together;
   (d) a pair of elongated fabric straps secured at one end to the end of the base pad opposite said fabric strap;
   (e) a loop in each of said elongated straps;
   (f) a pair of thick, soft, resilient pads, each having a cleft to be placed one on said base pad and the other on the first pad; and
   (g) means to fasten said pads in a compact unit with the impaled object positioned in said clefts.

4. The device according to claim 1 wherein when a ski pole having a basket is impaled in a body, non-resilient disks having clefts are placed between the body and the basket in the opening in the lower pad to help stabilize the ski pole and prevent further internal damage.

* * * * *